US008739634B2

(12) United States Patent
Ong et al.

(10) Patent No.: US 8,739,634 B2
(45) Date of Patent: Jun. 3, 2014

(54) FREEZE THAW DAMAGE RESISTANCE TESTING FOR CEMENTITIOUS COMPOSITIONS

(75) Inventors: Frank S. Ong, Solon, OH (US); James C. Smith, Cuyahoga Falls, OH (US); Eric Castner, Uniontown, OH (US); Heather See, Hiram, OH (US); Paul L. Pridemore, Willoughby, OH (US)

(73) Assignee: Construction Research & Technology GmbH, Trostberg (DE)

( * ) Notice: Subject to any disclaimer, the term of this patent is extended or adjusted under 35 U.S.C. 154(b) by 794 days.

(21) Appl. No.: 13/017,647

(22) Filed: Jan. 31, 2011

(65) Prior Publication Data

US 2012/0197547 A1 Aug. 2, 2012

(51) Int. Cl.
*G01N 3/00* (2006.01)
(52) U.S. Cl.
USPC .......................................................... 73/805
(58) Field of Classification Search
USPC .......................................................... 73/805
See application file for complete search history.

(56) References Cited

U.S. PATENT DOCUMENTS

| 6,112,599 | A | * | 9/2000 | Maki, Jr. .......................... 73/801 |
| 6,485,560 | B1 | | 11/2002 | Scherer et al. |
| 7,038,470 | B1 | | 5/2006 | Johnson |
| 7,435,766 | B2 | * | 10/2008 | Ong .............................. 523/223 |
| 7,551,058 | B1 | | 6/2009 | Johnson et al. |
| 2013/0139729 | A1 | * | 6/2013 | Ong et al. ...................... 106/697 |

OTHER PUBLICATIONS

Sun, Zhenhua and Scherer, George W.; "Effect of Air Voids on Salt Scaling and Internal Freezing"; Cement and Concrete Research; Feb. 2010, pp. 260-270; vol. 40, Issue 2.
Lin, Liwei, et al.; "A Micro Strain Gauge with Mechanical Amplifier"; Journal of Microelectrochemical Systems; Dec. 1997, pp. 313-321; vol. 6, No. 4.
Lindmark, Sture; "Mechanisms of Salt Frost Scaling of Portland Cement-bound Materials: Studies and Hypothesis"; 1998; Lund Institute of Technology, Division of Building Materials; Report TVBM 1017; Lund, Sweden.
Sommer, Von; Cement Research Institute, Vienna; "A New Method of Making Concrete Resistant To Frost and De-icing Salt"; Betonwerk und Fertigteil-Technik, Heft Sep. 1978.

* cited by examiner

*Primary Examiner* — Lisa Caputo
*Assistant Examiner* — Octavia D. Hollington
(74) *Attorney, Agent, or Firm* — Curatolo Sidoti Co., LPA; Joseph G. Curatolo; Salvatore A. Sidoti (57) ABSTRACT

An apparatus and method for predicting freeze-thaw durability of a cementitious composition specimen including cycling the specimen below and above the freezing point of water contained in the specimen and identifying the contraction and/or expansion of the specimen during the cycling.

18 Claims, 11 Drawing Sheets

FREEZE THAW DAMAGE RESISTANCE TESTING FOR CEMENTITIOUS COMPOSITIONS

This disclosure relates to a method for testing the freeze-thaw damage resistance of cementitious compositions.

It is well known that freezing and thawing cycles can be extremely damaging to water-saturated hardened cement compositions such as concrete. A known technique to prevent or reduce the damage done is the incorporation into the composition of microscopically fine air voids. The air voids are thought to function as internal expansion chambers to protect the concrete from freeze thaw damage by relieving the hydraulic pressure caused by an advancing freezing front in the concrete. The method used in the industry for artificially producing such air voids in concrete has been by means of air-entraining agents, which stabilize tiny bubbles of air that are entrapped in the concrete during mixing.

During freezing and thawing, either the cement paste or the aggregate or both may be damaged by dilation. In this process, stresses beyond the proportional limit may be produced which may cause permanent enlargement or actual disintegration. Dilation and associated stresses are believed to be due to: hydraulic pressure generated when growing ice crystals displace unfrozen water and cause it to flow against resistance to unfrozen portions of the mass; growth of capillary ice crystals; and, osmotic pressures brought about by local increases of alkali concentration caused by the separation of pure ice from the solution. The large number of closely spaced small air bubbles in air-entrained concrete have been thought to act as reservoirs for the relief of pressure developed within the freezing concrete and thus to relieve or avoid the high tensile stresses that lead to failure.

Additions of 4 to about 6% purposefully entrained air in concrete, with a 1½ inch (38-mm) maximum-size aggregate, greatly increase resistance to freezing and thawing. As the maximum coarse-aggregate size is decreased, the amount of entrained air is typically increased, such that as an example, concrete with a maximum aggregate size of ¼ inch (6 mm) will have an entrained-air content between 8 and 10%.

Cementitious composition materials such as cement paste may contain capillary pores on the order of 0.01-10 microns (10-10,000 nm), and gel pores on the order of less than 0.0005-0.01 microns (0.5-10 nm). Cementitious materials, such as air entrained cement pastes, may contain air voids on the order of 10-1000 microns.

As a result of the minute size of the pores and the presence of dissolved ions, water held in the pores of the hardened cementitious material will not have the properties of bulk water. In very small pores, the freezing point of water is depressed due to size constraints and the surface energy of the water-matrix interface. However, if the temperature drops low enough, then ice still forms.

The volume of ice is greater than the volume of an equivalent amount of water according to the formula: V(ice)=1.09 V(water). The thermal expansion of ice is approximately five times larger than that of hardened cement paste, resulting in cracking of the concrete upon thawing.

According to the Powers Hydraulic Pressure Model (1945), a pressure head is generated due to ice forcing water into the pores, dependent upon viscosity of the water solution and the pore size. If water is forced into air voids rather than capillary or gel pores, then stress is reduced and damage to the concrete is avoided.

In an air entrained specimen, as the temperature decreases, water travels to the air void due to the pressure buildup and the difference between the matrix air interface energy and the matrix-water interface energy. The water freezes in the void, and the paste shrinks due to the coefficient of thermal expansion. Shrinkage does not cause structural damage, because the hardened cement paste is strong in compression, although low in tensile strength.

Additions of air to a given concrete mix, however, will result in lower strength of the hardened concrete. The compressive strength of concrete will decrease by about 5% for each percent of entrained air when concrete of a given water/cement ratio are compared.

Other techniques and/or additives to prevent or reduce freeze-thaw damage in cementitious compositions are investigated from time to time, and a test has been needed to determine in a short time frame whether cementitious specimens prepared according to the experimental techniques actually exhibit freeze-thaw damage resistance.

ASTM Standard C666 provides two procedures for conducting tests to determine the resistance of concrete specimens to rapid freezing and thawing in water, and to rapid freezing in air and thawing in water. The concrete specimens for the ASTM C666 test are generally on the order of 3"×4"×16" (7.62 cm×10.16 cm×40.64 cm), and specifically are not less than 3 inches (7.62 cm) or more than 5 inches (12.7 cm) in width or height or diameter and not less than 11 inches (27.94 cm) or more than 16 inches (40.64 cm) in length. The relative dynamic modulus of each specimen is measured initially at −2° F. (−18.8° C.) to +4° F. (15.5° C.) of the target freeze-thaw temperature and to the tolerances required in ASTM C 215, and the relative dynamic modulus test is repeated periodically during the freeze-thaw cycling, with specimens being removed from the freeze-thaw apparatus at intervals not exceeding 36 cycles.

A nominal cycle consists of lowering the temperature of the specimens from 40° F. to 0° F. (+4.4° C. to −17.8° C.) and then raising the temperature from 0° F. to 40° F. (−17.8° C. to +4.4° C.) in not less than 2 or more than 5 hours. The period of transition between freezing and thawing cycles is not more than 10 minutes.

These procedures require that the test be continued until the specimens have sustained 300 cycles of freezing and thawing (approximately 25 to 60 days) or until the dynamic modulus of elasticity has reached 60% of initial modulus. A measure of the durability, the durability factor DF, may then be calculated from the equation:

$$DF = \frac{PN}{M}$$

where
P=relative dynamic modulus of elasticity at N cycles (%),
N=number of cycles at which P reaches the specified minimum value for discontinuing the test or the specified number of cycles at which the exposure is to be terminated, whichever is less, and
M=specified number of cycles at which the exposure is to be terminated.

The standard states that the methods are not intended to provide a quantitative measure of the length of service that may be expected from a specific type of concrete under field conditions.

The result of the ASTM C666 test is a single data point, pass or fail. Because of the standard deviation of individual specimens, it is necessary to conduct the tests on sets of specimens.

A diagnostic test to predict the freeze-thaw durability of cementitious materials is provided that is much more rapid and less material intensive than ASTM C666, yet provides excellent correlation with ASTM C666 test results. Further, the subject freeze-thaw test system provides the ability to observe specimen performance through each freeze-thaw cycle.

A method is provided for predicting freeze-thaw durability of a cementitious composition specimen comprising:
  a) providing a cured specimen;
  b) contacting the specimen with a microstrain gauge sensor capable of detecting specimen size changes;
  c) soaking the specimen in water;
  d) preventing moisture loss from the specimen during temperature cycling;
  e) equilibrating the specimen in a test chamber at an initial temperature above the freezing point of water;
  f) conducting temperature cycling by:
    i) cooling the test chamber interior containing the specimen from the initial temperature to a temperature below the freezing point of water contained in the specimen micropores;
    ii) holding temporarily the test chamber interior at the lowest temperature achieved by said cooling;
    iii) warming the test chamber interior to a temperature above the freezing point of water;
    iv) holding temporarily the test chamber interior at the highest temperature achieved by said warming;
  g) optionally repeating said temperature cycling;
  h) capturing information from the microstrain gauge sensor during the temperature cycling to identify microstrain experienced by the specimen as a function of at least one of test chamber interior temperature or specimen temperature; and,
  j) converting said sensor information to specimen microstrain data in at least one of a machine readable or operator readable format representing specimen contraction and/or expansion.

The subject test method can determine the freeze-thaw resistance of cementitious compositions for multiple specimens. Once the specimens have been conditioned for the test, the subject test method provides a rapid determination of the freeze-thaw resistance of the cementitious compositions within hours, rather than months as with prior industry standard tests.

A freeze-thaw test system is provided comprising:
  a test chamber for housing at least one cementitious composition specimen;
  a strain gauge sensor attached to each at least one respective specimen;
  a temperature sensor disposed within the test chamber and a second temperature sensor disposed within at least one specimen;
  data acquisition means in communication with each of the strain gauge sensors and temperature sensors; and
  a processor for process control and data processing and/or storage, operatively connected to the data acquisition means.

The freeze-thaw test system comprises a data acquisition and recording system that measures, analyzes and records cementitious specimen strain data caused by changes in a physical dimension of the specimen (due to shrinkage and/or expansion) over time and during changes in temperature.

Figure 1:
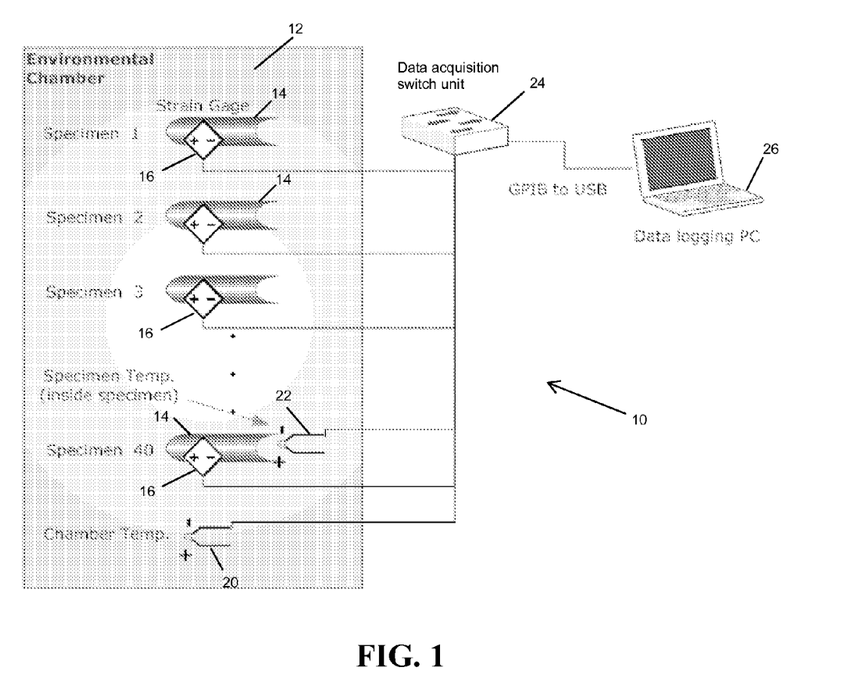
FIG. 1 is a schematic diagram of an embodiment of the freeze-thaw test system.

In one embodiment, depicted by FIG. 1, the freeze-thaw test system 10 comprises the following main hardware elements: An environmental chamber 12 for housing 1 to 40 or more cementitious material specimens 14 to be tested; one to 40 (or more) strain gauge sensors 16 (such as microstrain sensors), each strain gauge sensor 16 being attached, such as being bonded, to one respective cementitious specimen 14; a plurality of thermocouples 20, 22 (temperature sensors); a data acquisition switch unit 24 for collection of data; and a processor 26 such as a computer for process control and data storage, operatively connected to the data acquisition switch unit 24. The data acquisition switch unit 24 is in communication with each of the microstrain gauge sensors 16 and temperature sensors 20, 22, optionally via an electrical interference reduction device (not shown).

The environmental chamber 12 may be adapted to house the cementitious specimens 14 in a gas such as air or in a liquid, such as water, an aqueous solution, or an organic liquid, at temperatures capable of cycling from above freezing, such as about 10° C., to below freezing, such as about minus 31° C. In one embodiment, foil strain gauge sensors 16, such as those available from Vishay Americas, Inc., Shelton, Conn., are glued or bonded to cylindrical cementitious specimens 14 in order to measure the amount of strain that is being placed on the specimens by the cycling of the temperature in the environmental chamber 12. In certain embodiments, the cementitious specimens are on the order of about 10 ml in volume. The glued strain gauges 16 may further be coated, such as with a nitrile rubber, to seal them from the environment in the chamber 12.

At least one thermocouple 20 may be positioned within the environmental chamber 12 to measure the temperature of the chamber outside of the cementitious specimens 14 at least during the temperature cycles, and a thermocouple 22 is positioned within the interior of at least one cementitious specimen 14, to measure the temperature of the specimen at least during the temperature cycles.

The strain gauges 16 and thermocouples 20, 22 may communicate with the data acquisition switch unit 24 wirelessly or through a wired connection, optionally utilizing a shielded multiconductor cable connected through terminal blocks and optionally a multiplexer module. Electronic noise or interference in the signals from the strain gauges and/or the thermocouples may be reduced by use of a resistor, a backplane, or a signal conditioning interface, connected for example between the gauges and the data acquisition switch unit 24, for increased accuracy. Data may be transmitted from the data acquisition switch unit 24, such as those available from Agilent Technologies, Inc. of Palo Alto Calif., to the computer 26 via a PCI GPIB card, available from Keithley Instruments, Cleveland, Ohio.

The freeze-thaw test system is capable of measuring, analyzing and recording data for multiple specimens simultaneously, depending upon the number of data channels available on the data acquisition switch unit 24 or units utilized.

In one embodiment, the software executed by the freeze-thaw test system is written in LabVIEW software as a stand-alone executable program. By way of example but not limitation, the data may be acquired by and read from the data acquisition switch unit at a rate of one sampling of each specimen 14 every 1 second to 30 minutes, typically every 10 to 60 seconds, however this is an adjustable, operator defined value. The raw voltage values from the strain gauge sensors 16 are converted to units of strain based upon a conversion formula and a gauge factor supplied by the user during setup of the test run.

The data may be recorded to two files, raw data and averaged data. The raw data may be formatted according to date, time, chamber temperature, specimen temperature and specimen strain. Averaged data may be formatted according to specimen temperature and specimen strain. A file may be saved each time the system starts recording. The system stops recording when the operator actuates a "Stop Recording" command.

Figure 2:
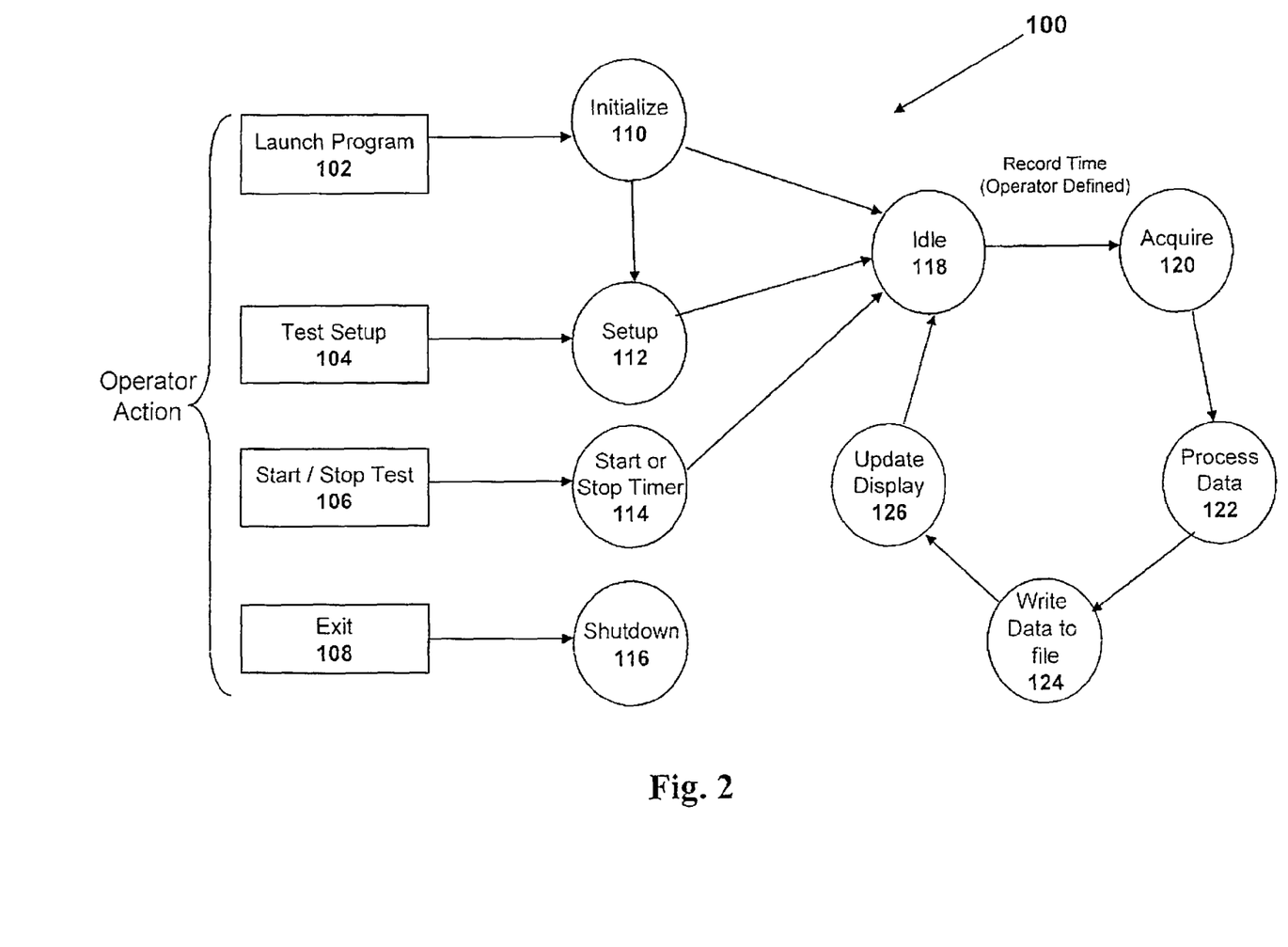
FIG. 2 is a flow chart of the operation of one embodiment of the freeze-thaw test system.

As shown in the high level process flow of the state machine depicted in FIG. 2, the freeze-thaw test system data capture 100 may commence when the operator launches the program 102 to initialize the software program 110. If the appropriate initialization file is not present, then test run setup 104 is prompted, or the operator can actuate setup 104 before initializing the program 110.

System setup 112 allows the operator to characterize each data channel (associated with a respective strain gauge sensor 16) by assigning a specimen identifier (such as a name, number and/or alphanumeric code) and a gauge factor. The operator may specify the test description, a run log file save folder and the recording interval. The operator may also select which specimen 14 is visible on a display, and may start or stop test recording 106 which may start or stop the timer 114. When the operator exits the system 108, the program may be shut down 116.

Figure 4:
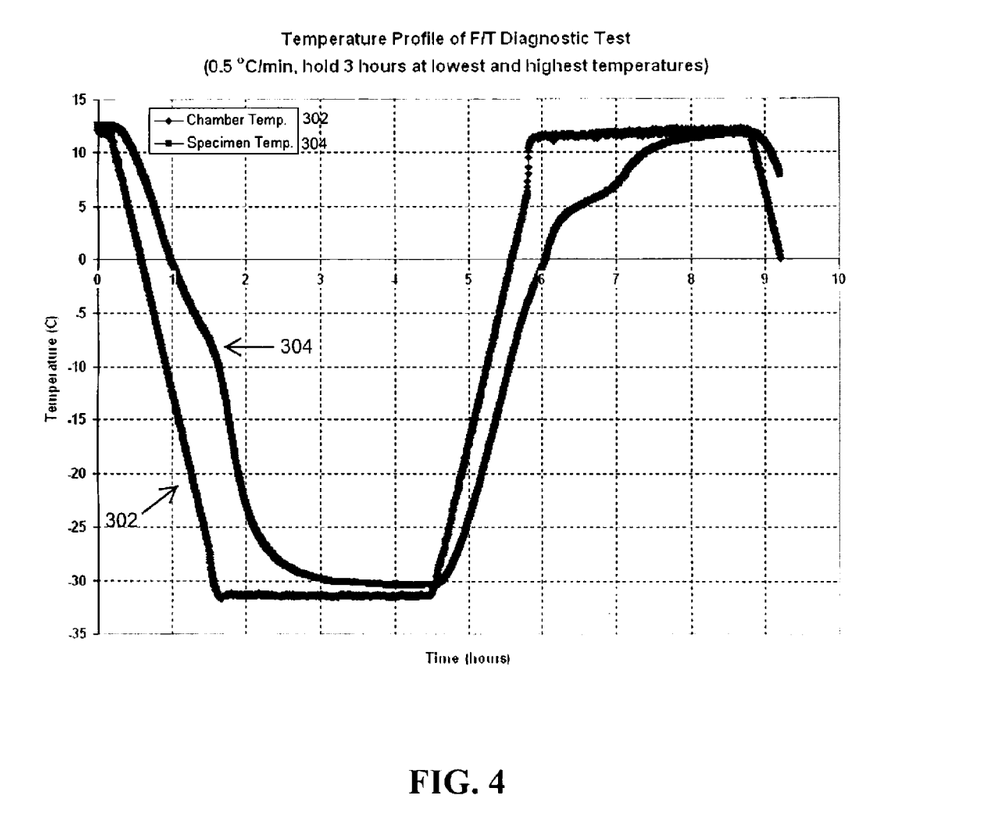
FIG. 4 is a graphical representation of an illustrative temperature profile of one embodiment of the subject freeze-thaw diagnostic test.

After initialization 110 and/or setup 112, the system may be in an idle state 118 until the operator defined record time is reached. This is typically when the environmental chamber 12 begins temperature cycling from a chamber temperature above freezing, such as about 10° C., to a temperature below the freezing point of water contained in the specimen, such as about minus 31° C., and back, for example but not by way of limitation according to a temperature profile such as is shown in FIG. 4, described below. The system then begins to acquire data 120, process the data 122, write the data to the log file 124, and update the system display 126.

The computer 26 screen may display, inter alia, data for one specimen 14 at a time, the specimen name (as defined in setup 112), the current strain value for each specimen on the display, historical strain values (both raw and average) for each specimen on a graph verses specimen temperature, current date and time, the test duration (how long it has been since recording started), indicate recording in progress, countdown time to next recording such as with a progress bar, and raw data for diagnostic purposes.

After initializing 110, the freeze-thaw test system program acquires, processes, displays, and records the temperature data in a loop that continues while the program is recording. In one exemplified embodiment, during the acquire state 120, values are acquired from the two temperature sensors 20, 22 and forty strain gauges 16. As depicted in the flow chart of FIG. 3, the process data state 122 may include conversion and manipulation of the data acquired 202 as follows.

Figure 3:
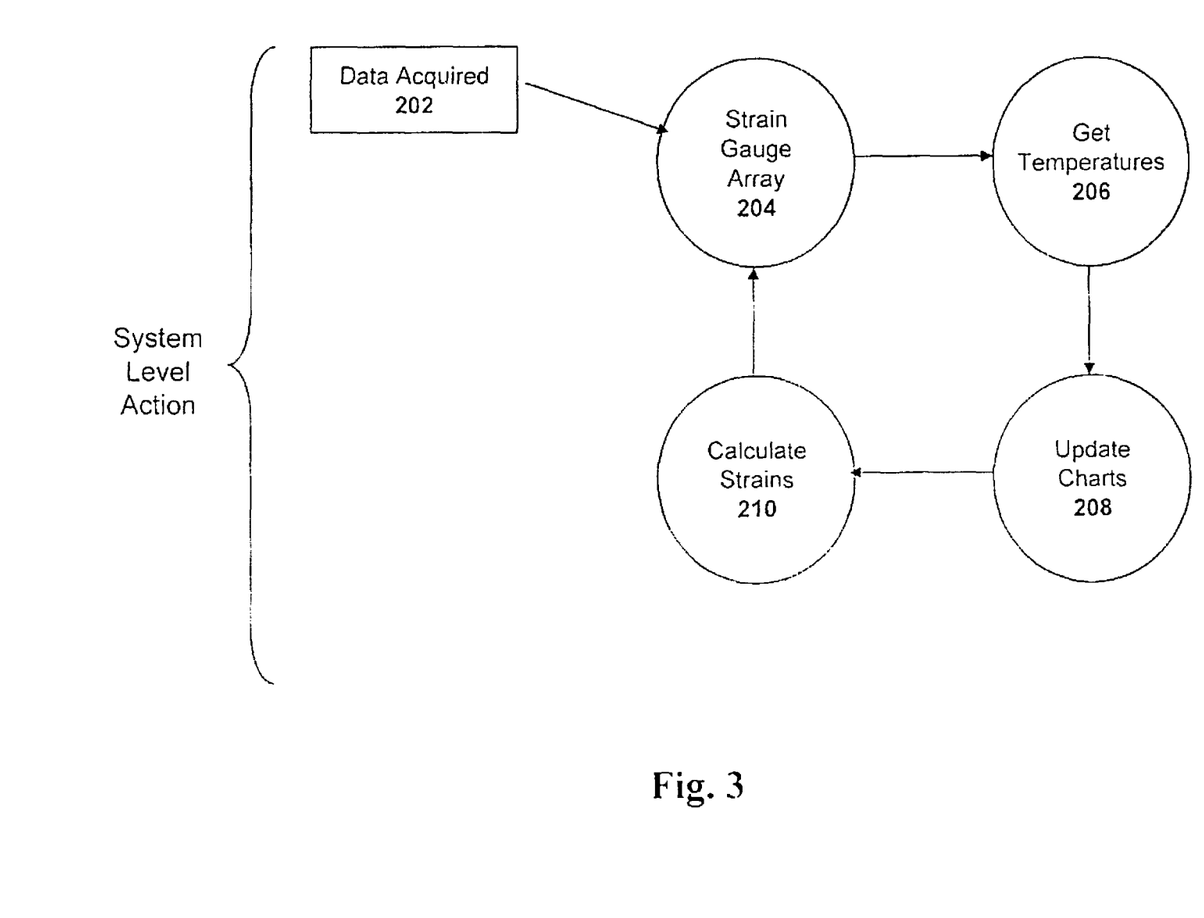
FIG. 3 is a flow chart of one aspect of the operation of one embodiment of the freeze-thaw test system.

Strain gauge values 204. Raw data acquired by the data acquisition unit 24 is returned as the number of strain sensor channels that were read, the time that the data was acquired, and the voltages per channel, in certain embodiments a 2D array of channel number and voltage reading pairs.

Get temperatures 206. The test data is updated with the current temperatures, the time the data was acquired, and a determination if there has been a 1 degree change from the last averaged data recording. The raw voltages are converted to real temperature (degrees C.) based on the thermocouple type.

The first temperature value acquired may be from the temperature thermocouple 20 disposed within the interior of the environmental chamber 12, and the second temperature value may be acquired from the temperature thermocouple 22 disposed within the interior of a control cementitious specimen 14. The values acquired by the data acquisition switch unit 24 are converted from the actual mV thermocouple reading into degrees C.

Update charts 208. In order to check if there has been a one degree change in the control specimen temperature, the current temperature is subtracted from the last temperature. If the absolute value of the difference is greater than 1, (that is, if there has been a 1 degree C. change), the data charts are updated to record this change.

The temperature data may be displayed 126 in text and/or on a graph, and the temperature data may be written to the two raw data and averaged data files. In the raw data file, the temperatures acquired from both thermocouples 20, 22 may be recorded with, for example, at least two digit precision (i.e. to the hundredths place), the record interval having been specified by the operator in setup 112. In the average (historical) data file, the specimen temperature may be recorded, for example, with two digit precision when there is a one degree change in the control specimen temperature. The average (or historical) specimen temperature is a value defined at this point in the process for each specimen 14 as the temperature of that specimen at the last one degree temperature change.

Calculate Strains 210. The strain gauge data for each cementitious specimen 14 may be manipulated as follows. The raw voltage for each strain gauge 16 is acquired. If the recording has started, the baseline voltage is updated with the current voltage reading. The change in voltage is converted to the strain value based on the appropriate gauge factor. In this embodiment, the strain was calculated according to formula (1):

$$\epsilon = 0.0024(\Delta V_m)/G_F \qquad (1)$$

where $\epsilon$ = strain (in/in);

$\Delta V_m$ = change in output voltage (current voltage measurement minus initial voltage measurement (VDC); and $G_F$ = gauge factor of the strain gauge (based on the particular manufacturing lot of the gauge material).

Test Procedure

The freeze thaw durability of cementitious materials was tested according to one embodiment of the subject test method. The microstrain based freeze-thaw test method results exhibit excellent correlation to the industry accepted ASTM Standard C666 test results for cementitious samples having at least about a 0.5 water to cement (W/C) ratio, while requiring only a fraction of the cementitious material for testing and providing results in days rather than months.

The microstrain freeze-thaw test method for predictive durability performance may utilize real-time data collection and analysis of multiple specimens simultaneously through the use of micro-strain measurement during at least one cooling (i.e. freezing) and optionally one warming or thawing temperature cycle, typically for multiple freeze-thaw cycles.

The temperature profile of the freeze-thaw test method as shown in FIG. 4, in one embodiment reduces the temperature of an environmental test chamber 12 from a chamber temperature indicated by curve 302 of about 10° C. to minus 31° C. at a rate of 0.5° C. per minute, holds at the lowest temperature achieved, for example, for 3 hours, and then increases the temperature of the chamber 12 at a rate of 0.5° C. per minute, holding at the highest temperature achieved, for example, for 3 hours, and then repeating the cycle. In other embodiments, the temperature of the test chamber 12 may be reduced and/or increased at a rate of about 0.1° C. to about 1° C. or more per minute. The specimen temperature indicated by curve 304, as measured by thermocouple 22 disposed within the control specimen 14, lags the chamber temperature as measured by thermocouple 20 disposed within the chamber. The hold period is used to allow the specimen temperature to equilibrate with, or reach, the chamber temperature, and thus may vary based upon the specimen composition, number of specimens, and chamber characteristics. The paths of the two profiles begin to diverge at about minus 5° C. to minus 7° C., when ice has begun to form in the specimen 14, the freezing point of water being depressed in the cementitious specimen as discussed above.

Specimens 14 within the test chamber are fitted with strain gauge sensors 16 capable of detecting micro-strain differentials, based on the changes in a dimension of the specimens due to shrinkage and/or expansion as a function of temperature.

The test method captures individual micro-strain data points at varying time intervals as desired, as well as calculates average micro-strain at 1° C. temperature increments. This predictive durability test also provides insight into the mechanisms of resistance and/or failure during freeze-thaw distress. A real-time display or computer may allow the operator to see the precise point of water-to-ice transition, and its effect on shrinkage or expansion of the individual test specimens.

In certain embodiments, test specimens for this method may be produced using 800 g cementitious paste batches at a 0.55 water-to-cement ratio. This method also works with mortars and screened concrete specimens, such as are produced at a 0.55 water-to-cement ratio, in which the aggregate is removed prior to testing of the residual paste or mortar. In certain embodiments, the cementitious materials are placed into 10 ml syringes under light vibration to eliminate large air pockets and "bug holes" internally and on the outer surfaces. Each resultant specimen is approximately 1.5 cm diameter×6 cm length and weighs approximately 15-25 grams depending on constituent materials.

In some embodiments, test specimens may be moist-cured at about 32° C. (90° F.) for fourteen (14) days prior to testing, in other embodiments, at about 70° F. (21.1° C.) for about 28 days. The remaining processes are conducted at ambient lab/environmental test chamber conditions. Individual microstrain gauges are attached to each test specimen and all specimens are pre-soaked in sealed centrifuge tubes with distilled water for at least 6 hours, typically about 18-24 hours or longer, prior to testing, to simulate conditions in the open environment for water-soaked cementitious material. At the conclusion of the pre-soak period, free water is drained from the specimen tubes and the tubes are resealed to prevent moisture loss in the specimens during cycling.

Specimens may then be equilibrated in the test chamber to 10° C. (50° F.) before starting the temperature cycle profile and data collection. In certain embodiments, the test may be conducted in air at 100% humidity. Predictive performance can be acquired within 6-9 hours from the start of data collection.

The cementitious compositions to be tested generally comprise hydraulic cement. Water is added to form the cementitious composition into a paste. The cementitious composition may include mortars, grouts, shotcrete, concretes or any other composition which comprises cement. The applications for the disclosed cementitious compositions include flatwork, paving (which is typically difficult to air entrain by conventional means), vertical applications, precast poured cement compositions and articles formed from cementitious compositions.

The test is conducted on cementitious compositions that will generally be exposed to the environment; that is, the cementitious composition will be in an environment exposed to weathering, water saturation, and freeze-thaw cycling.

The hydraulic cement can be a portland cement, a calcium aluminate cement, a magnesium phosphate cement, a magnesium potassium phosphate cement, a calcium sulfoaluminate cement or any other suitable hydraulic binder. Aggregate may be included in the cementitious composition. The aggregate, by way of example but not limitation, may include silica, quartz, sand, crushed marble, glass spheres, granite, limestone, calcite, feldspar, alluvial sands, any other durable aggregate, and mixtures thereof.

When the cementitious composition to be tested contains large aggregate, the aggregate may be screened out of the cementitious mixture prior to curing, so that the corresponding cementitious paste or mortar is subjected to the freeze-thaw test method.

The cementitious composition may contain other additives or ingredients and need not be limited to the formulations detailed herein. Cement additives that can be added independently include, but are not limited to: air entrainers, aggregates, pozzolans, dispersants, set and strength accelerators/enhancers, set retarders, water reducers, corrosion inhibitors, wetting agents, water soluble polymers, rheology modifying agents, water repellents, fibers, dampproofing admixtures, permeability reducers, pumping aids, fungicidal admixtures, germicidal admixtures, insecticide admixtures, finely divided mineral admixtures, alkali-reactivity reducer, bonding admixtures, shrinkage reducing admixtures, and any other admixture or additive that does not adversely affect the desired properties of the cementitious composition. The term dispersant is also meant to include those chemicals that also function as a plasticizer, high range water reducer, fluidizer, antiflocculating agent, or superplasticizer for cementitious compositions. The cementitious compositions need not contain one of each of the foregoing additives.

EXAMPLES

Samples 1-2

Cementitious paste compositions were prepared by mixing the components listed in Table I, below. The non-air entrained Sample 1 (Non-AE) contained no air entraining or freeze-thaw durability additive, and the air entrained Sample 2 (AE) contained a commercial air entraining admixture.

TABLE I

| Sample | Cement (g) | Sand/ Stone | Water (g) | W/C | MicroAir ® (ml) | 400 ml (g) | Air (%) |
|---|---|---|---|---|---|---|---|
| 1 Non-AE | 2068.00 | 0.00 | 849.60 | 0.41 | 0.00 | 782.00 | −0.9% |
| 1 Non-AE | 2068.00 | 0.00 | 849.60 | 0.41 | 0.00 | 776.70 | −0.2% |
| 1 Non-AE | 2068.00 | 0.00 | 849.60 | 0.41 | 0.00 | 780.80 | −0.8% |
| 2 AE | 800.00 | 0.00 | 328.00 | 0.41 | 1.00 | 714.50 | 7.8% |
| 2 AE | 800.00 | 0.00 | 328.00 | 0.41 | 1.00 | 716.50 | 7.6% |
| 2 AE | 800.00 | 0.00 | 328.00 | 0.41 | 1.00 | 715.40 | 7.7% |

Pass-fail characteristics of test specimens will be explained with respect to Samples 1 and 2, and FIGS. 5 through 8.

As the specimens are cooled from about 10° C., the micro-strain sensors indicate that the cementitious material specimens begin to contract linearly at a rate corresponding approximately to the coefficient of thermal expansion for concrete. At approximately minus 5° C., ice begins to form in the specimens, and the temperature rebounds slightly due to heat of crystallization.

Figure 5:
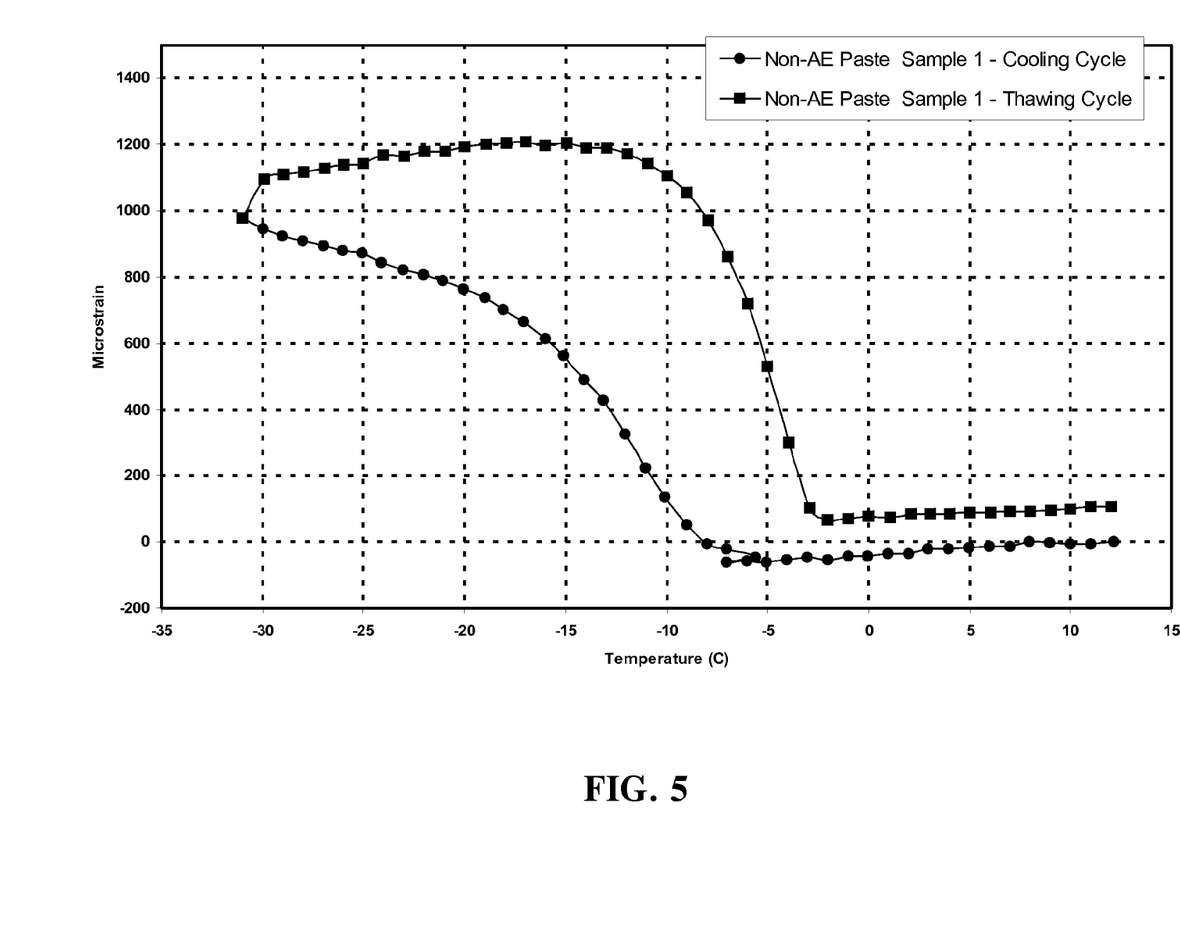
FIG. 5 is a graphical representation of cementitious composition freeze-thaw performance of one specimen as measured by micro-strain due to specimen size changes across a cooling and thawing temperature profile.
Figure 6:
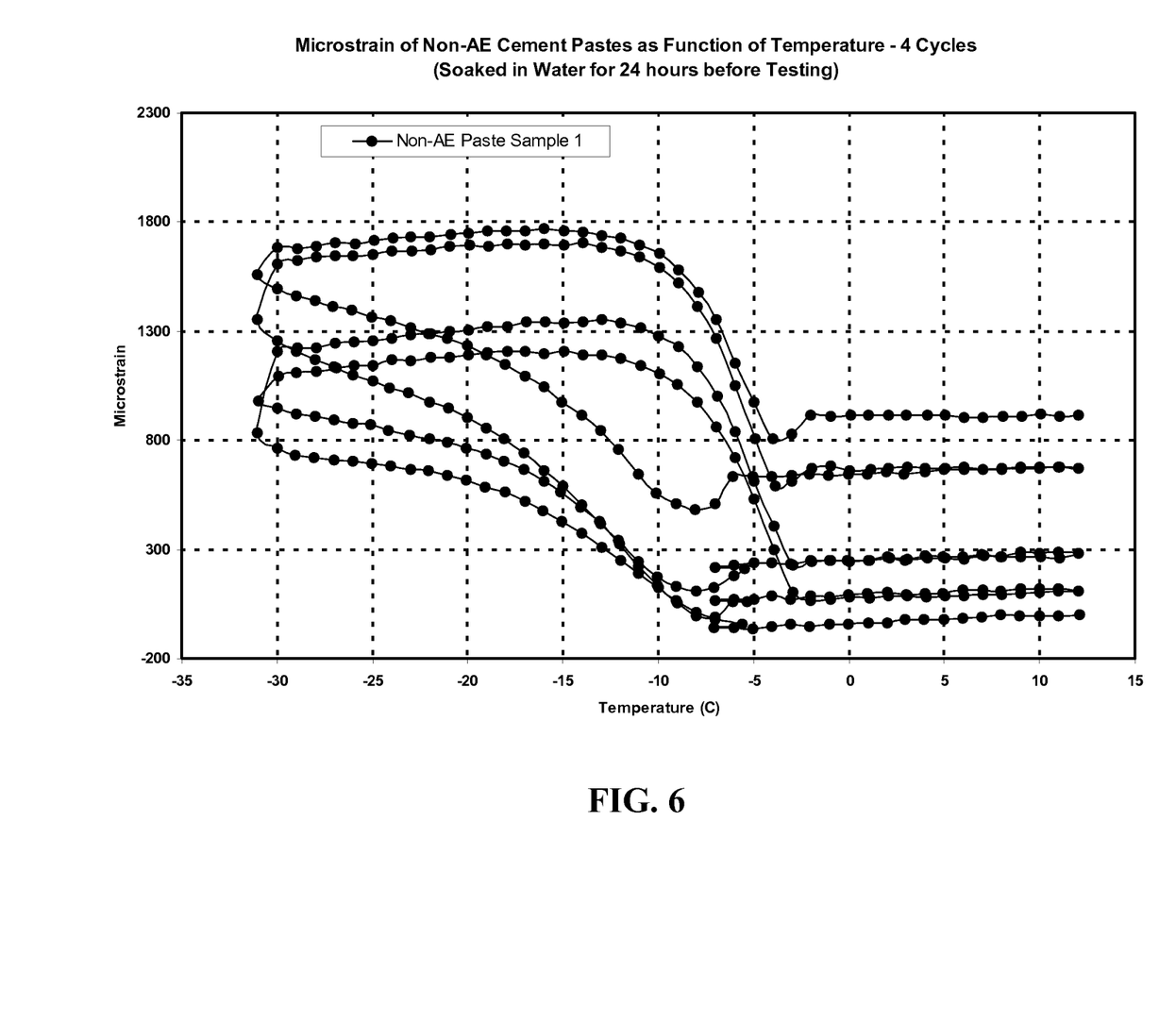
FIG. 6 is a graphical representation of cementitious composition freeze-thaw performance of one specimen as measured by micro-strain due to specimen size changes across multiple cycles of a cooling and thawing temperature profile.

As shown in FIGS. 5 and 6, for the non-air entrained Sample 1 specimen, when further cooling commenced, the micro-strain sensors indicated that the non-air entrained specimen began to expand as the temperature of the specimen decreased. It is theorized that the expansion is caused by expansion of water crystallizing to ice in micropores in the cementitious material, and to structural damage caused by such expansion.

As shown in FIGS. 5 and 6, when the temperature cycled to the warming mode, the micro-strain sensors indicated that the non-air entrained Sample 1 specimen at first continued to expand and then began to shrink, theoretically as ice within the pores began to melt, until all of the ice had melted at about minus 5° C. The specimen then began to expand linearly according to the thermal coefficient of cementitious material as it returned to 10° C. temperature. As shown in FIG. 6, in subsequent cycles, the same pattern repeated, except that the expansion of the specimen was more pronounced during cooling below minus 5° C., perhaps indicating that the structural damage to the specimens was cumulative.

Figure 7:
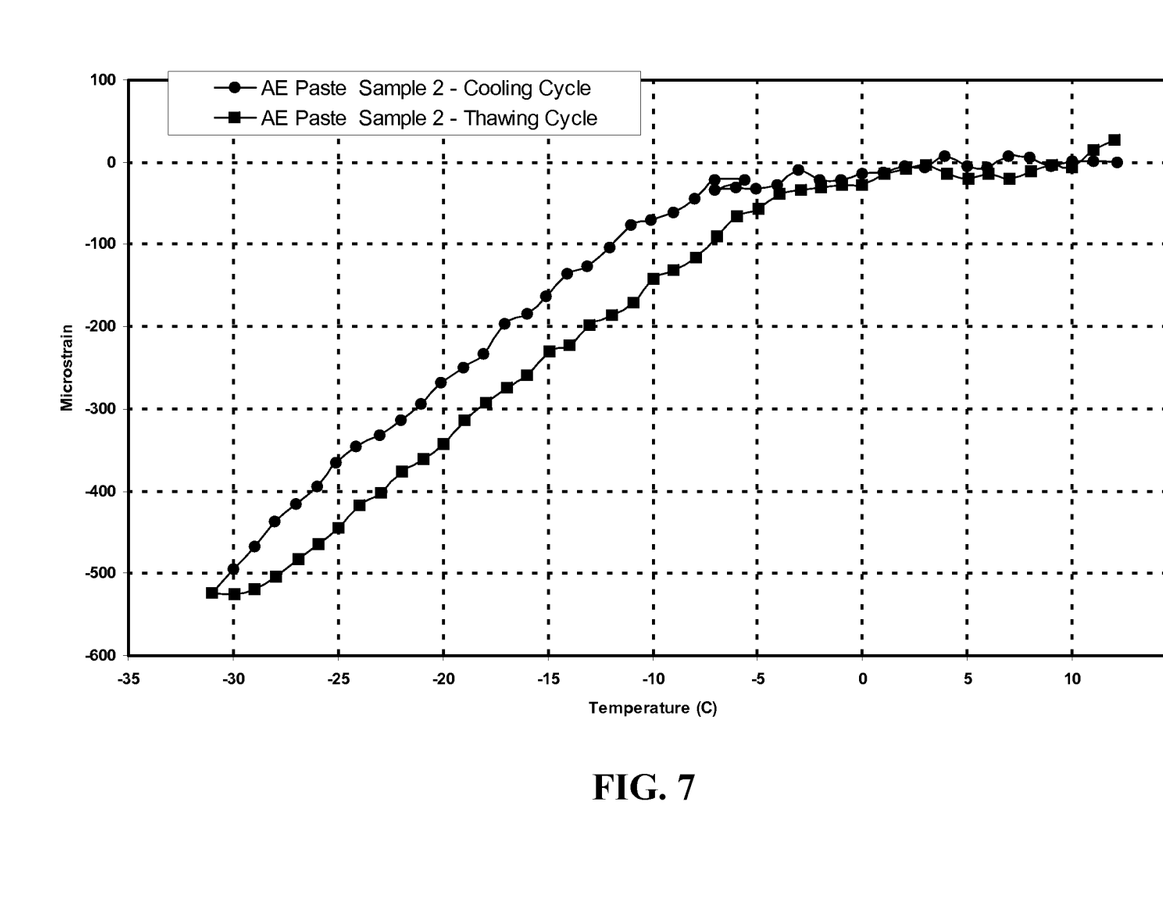
FIG. 7 is a graphical representation of cementitious composition freeze-thaw performance of one specimen as measured by micro-strain due to specimen size changes across a cooling and thawing temperature profile.
Figure 8:
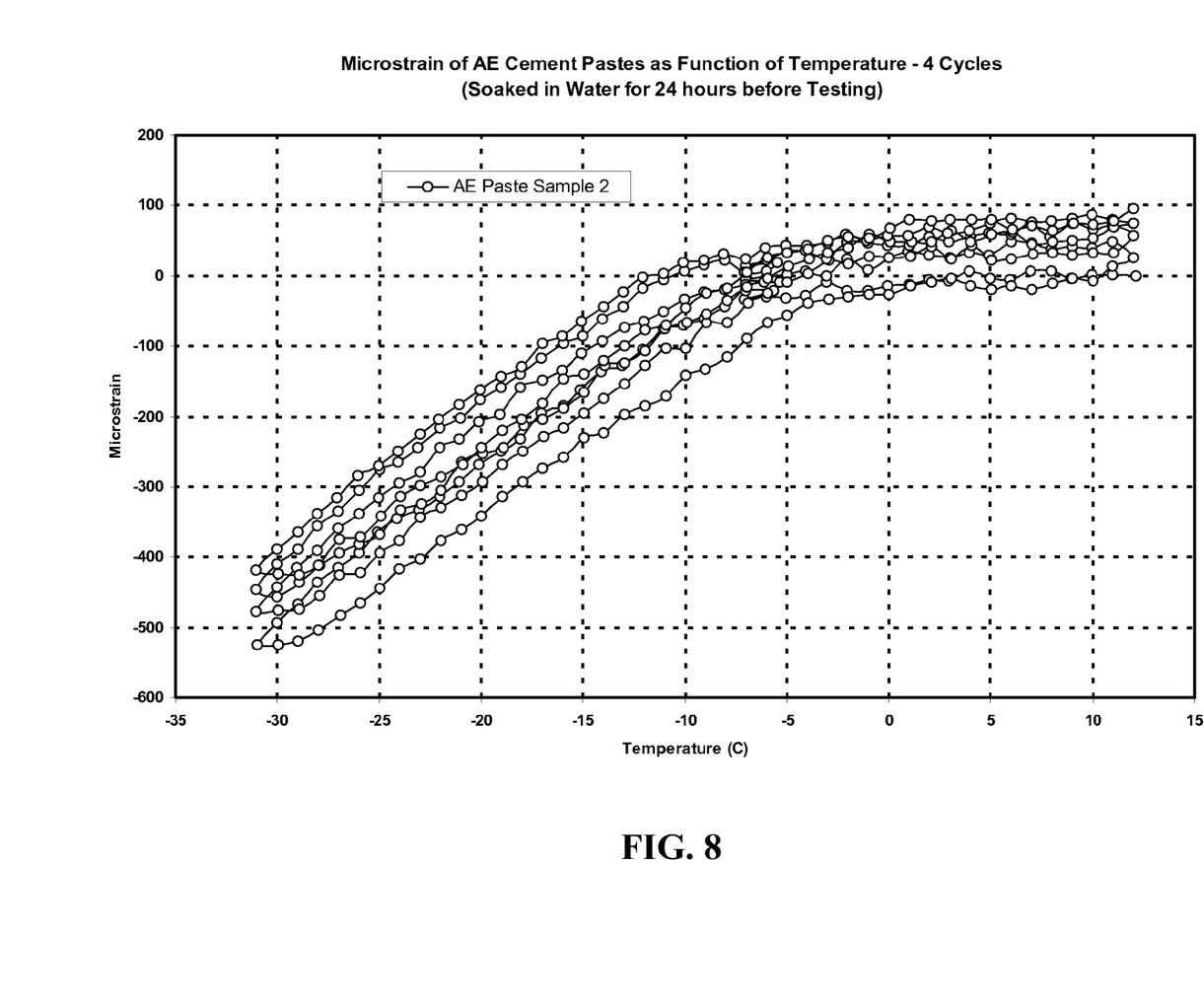
FIG. 8 is a graphical representation of cementitious composition freeze-thaw performance of one specimen as measured by micro-strain due to specimen size changes across multiple cycles of a cooling and thawing temperature profile.

As shown in FIGS. 7 and 8, for the entrained air Sample 2 specimen, after the linear contraction of the specimen to about minus 5° C., the specimen continued to contract at a rate corresponding to a composite coefficient of thermal expansion of the cementitious material and ice contained within its pores. As shown in FIGS. 7 and 8, when warming of the specimen commenced and proceeded, the air-entrained Sample 2 specimen expanded linearly, substantially at the same rate as it had contracted. As shown in FIG. 8, the behavior of the air entrained specimen in subsequent cycles followed the same cooling contraction and warming expansion characteristics as in the first cycle, indicating that the specimen remained substantially structurally identical through multiple freeze-thaw cycles.

Samples 3-4

Cementitious compositions were prepared by mixing the components listed in Table II, below. The non-air entrained Sample 3 contained no air entraining or freeze-thaw durability additive, and the air entrained Sample 4 contained the commercial AE 90® air entraining admixture. The cementitious specimens had a cement factor of 517, and a water to cement ratio of 0.55.

TABLE II

| Sample No. | 3 | 4 |
|---|---|---|
| Admixture 1 AE 90 ® Dose (oz/cwt) | | 1.35 |
| Cement (lbs) | 28.7 | 28.7 |
| Total Cementitious (lbs) | 28.7 | 28.7 |
| Sand (lbs) | 76.4 | 71.6 |
| Total Stone (lbs) | 104.7 | 98.1 |
| Stone 1 (lbs) | 62.6 | 58.7 |
| Stone 2 (lbs) | 42.1 | 39.4 |
| Water (lbs) | 15.8 | 15.8 |
| Water/Cement | 0.55 | 0.55 |
| Sand/Aggregate Ratio | 0.44 | 0.44 |
| Air Content (%) | | |
| 5 Minutes | 1.3 | 7.2 |

Freeze Thaw Durability

Specimens for Samples 3 and 4 were obtained by screening a cementitious mortar from the concrete compositions to remove aggregate. The specimen for Sample 4 had an air content of about 7.8%. The screened specimens were held at 35° C. for 14 days, and were soaked in water for 4 days prior to conducting freeze thaw testing to simulate water-soaked environmental conditions.

Figure 9:
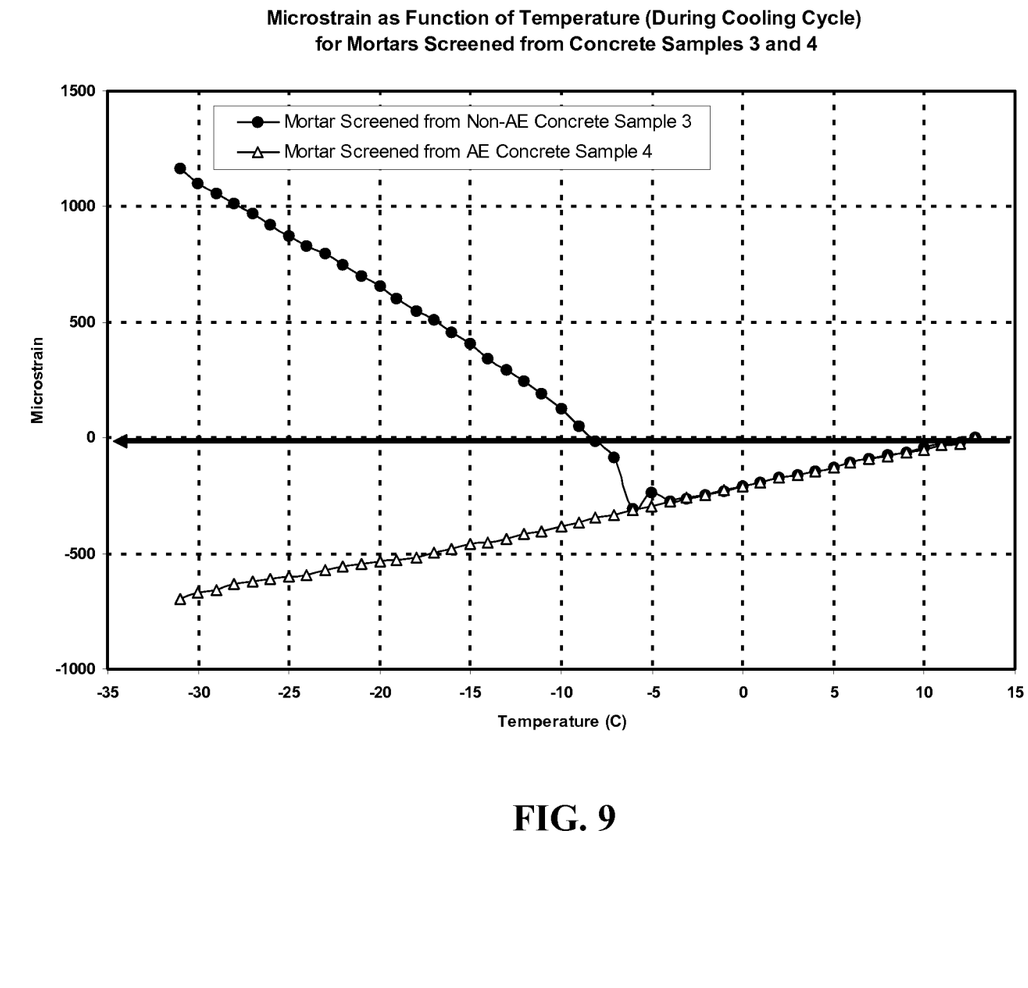
FIG. 9 is a graphical representation of the comparison of cementitious composition freeze-thaw performance of two specimens as measured by micro-strain due to specimen size changes across a cooling temperature profile.
Figure 10:
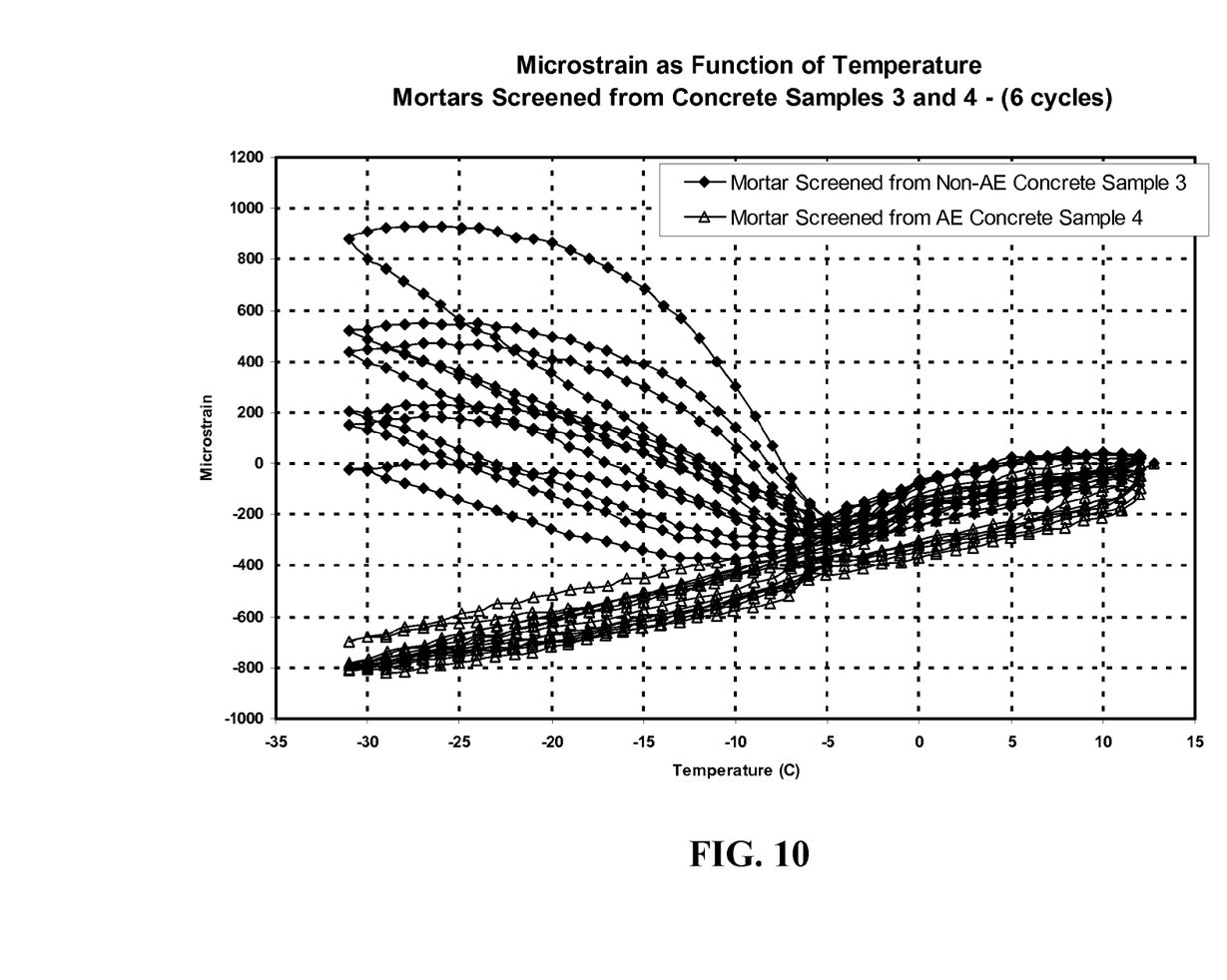
FIG. 10 is a graphical representation of the comparison of cementitious composition freeze-thaw performance of two specimens as measured by micro-strain due to specimen size changes across multiple cycles of a cooling and thawing temperature profile.

As shown in FIGS. 9 and 10, when the specimens were cooled from about 10° C., the micro-strain sensors indicated that the cementitious material specimens began to contract linearly at a rate corresponding approximately to the coefficient of thermal expansion for concrete.

In the non-air entrained Sample 3, when cooling continued, the micro-strain sensors indicated that the non-air entrained specimen began to expand as the temperature of the specimen decreased. As shown in FIG. 10, when the temperature cycled to the heating mode, the micro-strain sensors indicated that the non-air entrained specimen began to shrink, theoretically as ice within the pores begins to melt, until all of the ice had melted at about minus 5° C. The specimen then began to expand linearly according to the thermal coefficient of cementitious material as it returned to ambient temperature. As shown in FIG. 10, in subsequent cycles, the same pattern repeated, except that the expansion of the specimen was more pronounced during cooling below minus 5° C., perhaps indicating that the structural damage to the specimen was cumulative.

In the entrained air Sample 4, after the linear contraction of the specimen during cooling to about minus 5° C., the specimen continued to contract at a rate corresponding to a composite coefficient of thermal expansion of the cementitious material and ice contained within its pores. As shown in FIG. 10, when warming of the specimen commenced and proceeded, the air-entrained specimen expanded linearly, substantially at the same rates as it had contracted. As shown in FIG. 10, the behavior of the air entrained specimen in subsequent cycles followed the same cooling contraction and warming expansion characteristics as in the first cycle, indicating that the specimen remained substantially structurally identical through multiple freeze-thaw cycles.

Correlation studies with the existing ASTM C666 methodology have been conducted successfully. Cementitious materials of varying air-entrainment quality were tested in both C666 and the subject predictive micro-strain freeze-thaw test methodology, as demonstrated below.

Samples 5-11

Cementitious compositions were prepared by mixing the components listed in Table III, below, to achieve a cement factor of 517 and a water to cement ratio of 0.55. The non-air entrained Sample 11 (Non-AE) contained no air entraining additive, and the air entrained Samples 5 through 10 (AE) contained varying amounts of the commercial AE 90® air entraining admixture, or the commercial Micro Air® air entraining admixture, both available from BASF Admixture Systems, Cleveland, Ohio. Specimens of Samples 5-11 were tested according to both the ASTM C666 test, and the subject freeze-thaw test method.

As reported in Table III, Samples 5 and 8 contained an insufficient amount of air entraining additive to provide freeze-thaw resistance for those specimens, when tested according to ASTM C666. Samples 5 and 8 specimens contained only 3.4% air each, and failed after 36 cycles and 108 cycles, respectively. Sample 11 specimens, containing no air entraining additive, exhibited only 2.4% air, and failed in less than 36 cycles of ASTM C666 testing.

Figure 11:
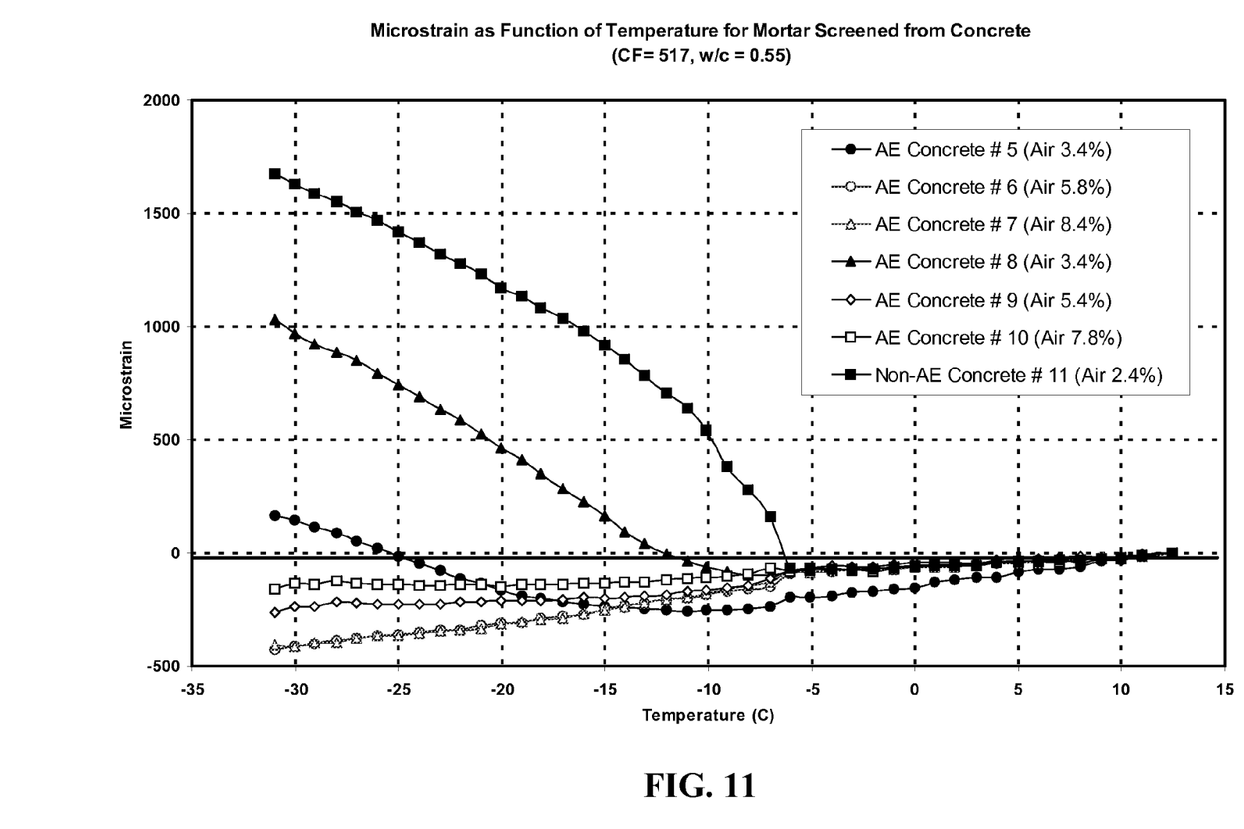
FIG. 11 is a graphical representation of cementitious composition freeze-thaw performance of multiple specimens as measured by micro-strain due to specimen size changes across a cooling temperature profile.

Cementitious composition specimens of 10 ml volume were prepared according to the subject predictive microstrain freeze-thaw test method procedures set forth above, screening the mortar fraction from concrete Samples 5-11. The cementitious specimens were tested according to the microstrain freeze-thaw test method protocol used for Samples 1-4. As shown in FIG. 11, the Sample 11 specimen, containing no air entraining additive, and the Samples 5 and 8 specimens containing only 3.4% air each, all failed the microstrain freeze-thaw durability predictive performance test. When cooling commenced after the initial ice formation at about minus 5° C., the micro-strain sensors indicated that the non-air entrained specimen of Sample 11 and the low air content entrained specimens of Samples 5 and 8 began to expand as the temperature of the specimens decreased.

As shown in FIG. 11, the test specimens of Samples 6, 7, 9 and 10, containing from 5.4% to 8.4% entrained air, continued to contract at temperatures below minus 5° C., at a rate corresponding to a composite coefficient of thermal expansion of the cementitious material and ice contained within their pores, for the duration of the cooling cycle to below minus 30° C. This correlated well to the ASTM C666 test results for Samples 6, 7, 9 and 10 as reported in Table III, which exhibited a relative dynamic modulus of 100% after 300 cycles.

The freeze-thaw durability predictive results of the present micro-strain freeze-thaw test method mirrored the actual results of the more cumbersome and time-consuming C666 method. Test specimens for the ASTM C 666 method can weigh between 15-25 pounds, the testing can take at least three months to complete, and the data collected offers no insight into the mechanism of resistance and/or failure for any test specimen.

The diagnostic micro-strain freeze-thaw test method for predicting the freeze-thaw durability of cementitious materials is much more rapid and less material intensive than ASTM C666. Once the specimens have been conditioned for the test, the subject test method provides a rapid determination of the freeze-thaw resistance of the cementitious compositions within hours.

The predictive micro-strain freeze-thaw test method further provides insight into the mechanisms of resistance and/or failure during freeze-thaw distress, allowing identification of the precise point of water-to-ice transition, and its effect on shrinkage or expansion of the individual test specimens.

In addition to testing cementitious materials containing air entraining admixtures for freeze-thaw durability, the freeze-thaw test method can test cementitious compositions that contain other freeze-thaw durability enhancing admixtures and additives.

It will be understood that the embodiments described herein are merely exemplary, and that one skilled in the art may make variations and modifications without departing from the spirit and scope of the invention. All such variations and modifications are intended to be included within the scope of the invention as described hereinabove. Further, all embodiments disclosed are not necessarily in the alternative, as various embodiments of the invention may be combined to provide the desired result.

The invention claimed is:

1. A method for predicting freeze-thaw durability of a cementitious composition specimen comprising:
   a) providing a cured specimen;
   b) contacting the specimen with a microstrain gauge sensor capable of detecting specimen size changes;
   c) soaking the specimen in water;
   d) preventing moisture loss from the specimen during temperature cycling;
   e) equilibrating the specimen in a test chamber at an initial temperature above the freezing point of water;
   f) conducting temperature cycling by:
      i) cooling the test chamber interior containing the specimen from the initial temperature to a temperature below the freezing point of water contained in specimen micropores;

TABLE III

Mortar Fraction of Concrete - With and Without Air Entraining Admixture
(CF = 517, W/C = 0.55)

| Sample No. | Cement | Sand Wt. (lb) | Stone | Water | S/A | W/C | AE 90® Vol. (ml) | Micro Air® Vol. (ml) | Air (%) | Slump (in) | # of cycles completed | D.M. % |
|---|---|---|---|---|---|---|---|---|---|---|---|---|
| 5  | 23.0 | 61.3 | 83.6 | 12.6 | 0.44 | 0.55 |     | 0.6 | 3.4 | 4.0 | 36   | Failed |
| 6  | 23.0 | 59.6 | 81.2 | 12.6 | 0.44 | 0.55 |     | 3.2 | 5.8 | 5.0 | 300  | 100 |
| 7  | 23.0 | 59.6 | 81.2 | 12.6 | 0.44 | 0.55 |     | 6.4 | 8.4 | 6.0 | 300  | 100 |
| 8  | 23.0 | 59.6 | 81.2 | 12.6 | 0.44 | 0.55 | 1.0 |     | 3.4 | 4.0 | 108  | Failed |
| 9  | 23.0 | 59.6 | 81.2 | 12.6 | 0.44 | 0.55 | 3.4 |     | 5.4 | 5.5 | 300  | 100 |
| 10 | 23.0 | 59.6 | 81.2 | 12.6 | 0.44 | 0.55 | 6.8 |     | 7.8 | 6.0 | 300  | 100 |
| 11 | 23.0 | 59.6 | 81.2 | 12.6 | 0.44 | 0.55 |     |     | 2.4 | 4.0 | <36  | Failed | ii) holding temporarily the test chamber interior at the lowest temperature achieved by said cooling;

iii) warming the test chamber interior to a temperature above the freezing point of water;

iv) holding temporarily the test chamber interior at the highest temperature achieved by said warming;

g) optionally repeating said temperature cycling;

h) capturing information from the microstrain gauge sensor during the temperature cycling to identify microstrain experienced by the specimen as a function of at least one of test chamber interior temperature or specimen temperature; and, j) converting said sensor information to specimen microstrain data in at least one of a machine readable or operator readable format representing specimen contraction or expansion.

2. The method of claim 1, wherein the specimen is moist-cured at a temperature above freezing for at least 14 days prior to testing.

3. The method of claim 1 wherein the specimen is soaked in water for at least 6 hours, optionally 18-24 hours, prior to testing.

4. The method of claim 1, wherein the specimen is sealed in a container to prevent moisture loss.

5. The method of claim 1, wherein the specimen is equilibrated at a temperature of at least about 10° C. before said conducting temperature cycling.

6. The method of claim 1, wherein said conducting temperature cycling comprises cooling the test chamber interior to at least about minus 30° C. at a rate of about 0.1° C. to about 1° C. per minute, optionally at 0.5° C. per minute, holding the test chamber interior at the lowest temperature achieved by said cooling for a time sufficient for specimen temperature to equilibrate to the test chamber interior temperature, warming the test chamber interior to at least about 10° C. at a rate of about 0.1° C. to about 1° C. per minute, optionally at 0.5° C. per minute, and holding the test chamber interior at the highest temperature achieved by said warming for a time sufficient for the specimen temperature to equilibrate to the test chamber interior temperature.

7. The method of claim 1, further comprising recording the specimen microstrain data as a function of at least one of test chamber interior temperature or specimen temperature, and optionally as a function of time.

8. The method of claim 1, further comprising graphing the specimen microstrain data as a function of at least one of the test chamber interior temperature or specimen temperature to determine if the specimen expands or contracts during cooling below onset of water freezing in the specimen.

9. The method of claim 1, further comprising measuring and optionally recording the temperature of the test chamber interior and of the specimen.

10. The method of claim 1, wherein multiple specimens are subjected to the method contemporaneously.

11. A freeze-thaw test system comprising:
a test chamber for housing at least one cementitious composition specimen;
a strain gauge sensor attached to each at least one respective specimen;
a temperature sensor disposed within the test chamber and a second temperature sensor disposed within at least one specimen;
data acquisition means in communication with each of the strain gauge sensors and temperature sensors; and
a processor for process control and data processing or storage, operatively connected to the data acquisition means.

12. The test system of claim 11, wherein the test chamber is adapted to cycle from a temperature above the freezing point of water, optionally about 10° C., to a temperature below the freezing point of water contained in at least one specimen micropores, optionally at least about minus 30° C.

13. The test system of claim 12, wherein the strain gauge sensor is a foil strain gauge sensor capable of attachment to the at least one specimen to measure the amount of strain that is placed on the specimen by the cycling of the temperature in the test chamber.

14. The test system of claim 11, wherein the data acquisition means is capable of acquiring data at a rate of one sampling of the at least one specimen every 1 second to 30 minutes, optionally every 10 to 60 seconds.

15. The test system of claim 11, capable of converting raw voltage values from the strain gauge sensors to units of strain.

16. The test system of claim 11, capable of testing the at least one specimen that is sealed in a container to prevent moisture loss.

17. The test system of claim 11, further comprising storage for data files containing information related to microstrain data of the at least one specimen as a function of at least one of test chamber interior temperature or specimen temperature, and optionally as a function of time.

18. The test system of claim 17, further comprising a display capable of displaying a graph of the specimen microstrain data as a function of at least one of test chamber interior temperature or specimen temperature to determine if the specimen expands or contracts during cooling below onset of water freezing in the specimen.

* * * * *